United States Patent [19]

Hobbs

[11] Patent Number: 5,675,098

[45] Date of Patent: *Oct. 7, 1997

[54] APPARATUS AND METHOD FOR THERMAL AND VIBRATIONAL STRESS SCREENING

[75] Inventor: Gregg K. Hobbs, Westminister, Colo.

[73] Assignee: Qualmark Corporation, Denver, Colo.

[ * ] Notice: The term of this patent shall not extend beyond the expiration date of Pat. No. 5,540,109.

[21] Appl. No.: 473,352

[22] Filed: Jun. 7, 1995

Related U.S. Application Data

[63] Continuation of Ser. No. 972,162, Nov. 5, 1992, Pat. No. 5,540,109.

[51] Int. Cl.$^6$ ............................................ G01N 29/04
[52] U.S. Cl. ................................................. 73/865.6
[58] Field of Search ............................ 73/663, 865.9, 73/865.6; 374/45–47, 50, 57; 62/125–127, 265, 266, 296, 331, DIG. 13, 49.1, 538, 539

[56] References Cited

U.S. PATENT DOCUMENTS

| | | | |
|---|---|---|---|
| H229 | 3/1987 | Phillips | 73/865.6 |
| 2,136,558 | 11/1938 | Manshel | 62/266 |
| 2,438,756 | 3/1948 | Larsen | 74/26 |
| 2,773,482 | 12/1956 | Dickie | 121/20 |
| 3,163,786 | 12/1964 | Dickinson | 310/27 |
| 3,217,531 | 11/1965 | Melton | 73/71.6 |
| 3,369,393 | 2/1968 | Farmer | 73/71.6 |
| 3,376,790 | 4/1968 | Matson | 91/234 |
| 3,381,526 | 5/1968 | Rastogi et al. | 374/47 |

(List continued on next page.)

FOREIGN PATENT DOCUMENTS

| | | | |
|---|---|---|---|
| A-948 463 | 4/1980 | European Pat. Off. | |
| 2 241 348 | 3/1975 | France | |
| 0144580 | 7/1986 | Japan | 374/57 |
| 160885 | 11/1964 | U.S.S.R. | |
| 1580198 | 7/1990 | U.S.S.R. | 73/663 |
| 1 367 285 | 9/1974 | United Kingdom | |
| 2 063 379 | 6/1981 | United Kingdom | |
| 2 211 268 | 6/1989 | United Kingdom | |

OTHER PUBLICATIONS

"Acoustic and Vibration Testing, Impact and Blast," Don G. VandeGriff et al., Bulletin 46, The Shock and Vibration Information Center, Naval Research Laboratory, Washington, D.C. (Aug. 1976).

"Mechanical and Pneumatic Shakers for Military Standard 781C," Wayne Tustin, *Proceedings—Institute of Environmental Sciences* pp. 242–248 (1977).

"Low Cost Mechanical Random Shakers," Douglas Nolan, *Proceedings—Institute of Environmental Sciences* pp. 238–241 (1977).

*Primary Examiner*—Robert Raevis
*Attorney, Agent, or Firm*—James R. Young; Scott B. Allison; Chrisman, Bynum & Johnson

[57] ABSTRACT

Environmental screening of products is facilitated and enhanced by employing screening compartments to subject products to differing environmental and functional conditions to expose latent defects in the products such as conductor weaknesses and discontinuities, component defects, material defects, and fragility. Within each compartment, products can be simultaneously subjected to various temperature and vibrational conditions as well as to stresses such as electric power cycling, voltage changes, frequency variations, and other functional stimuli. The thermal, vibrational, and other environmental and functional conditions created in each compartment are independently controlled and monitored from those conditions in other compartments. Products are readily transported between screening compartments, which can be adjacent each other, in order to rapidly subject the products to differing screening conditions while minimizing time and energy waste. Products can be visually and electronically monitored during the screening process to determine if the products are functioning as expected. The present invention reduces the level of time, manual intervention, cost, and energy required in order to evaluate product tolerance to differing environmental and functional conditions.

33 Claims, 8 Drawing Sheets

U.S. PATENT DOCUMENTS

| | | | |
|---|---|---|---|
| 3,686,927 | 8/1972 | Scharton | 73/71.6 |
| 3,836,098 | 9/1974 | Miyashita | 244/17.27 |
| 4,030,348 | 6/1977 | Fletcher et al. | 374/47 |
| 4,164,151 | 8/1979 | Nolan et al. | 73/663 |
| 4,181,025 | 1/1980 | Abstein, Jr. et al. | 73/665 |
| 4,181,026 | 1/1980 | Abstein, Jr. et al. | 73/665 |
| 4,181,027 | 1/1980 | Talbott, Jr. | 73/665 |
| 4,181,028 | 1/1980 | Talbott, Jr. | 73/665 |
| 4,181,029 | 1/1980 | Talbott, Jr. | 73/665 |
| 4,446,742 | 5/1984 | Thompson, Jr. et al. | 73/663 |
| 4,537,077 | 8/1985 | Clark et al. | 73/665 |
| 4,633,716 | 1/1987 | Martin | 73/663 |
| 4,735,080 | 4/1988 | Stehr | 72/427 |
| 4,735,089 | 4/1988 | Baker et al. | 73/663 |
| 4,739,622 | 4/1988 | Smith | 62/49.1 |
| 4,925,198 | 5/1990 | Ito et al. | 280/89 |
| 5,039,228 | 8/1991 | Chalmers | 73/865.6 |
| 5,195,384 | 3/1993 | Duesler, Jr. et al. | 73/865.6 |

APPARATUS AND METHOD FOR THERMAL AND VIBRATIONAL STRESS SCREENING

CROSS REFERENCE TO RELATED APPLICATION

This patent application is a continuation application of U.S. patent application Ser. No. 07/972,162 filed Nov. 5, 1992, now U.S. Pat. No. 5,540,109.

BACKGROUND OF THE INVENTION

The present invention relates generally to the screening of products for the presence of latent defects which would be exposed by normal usage and transportation during the life of the products. More particularly, the present invention relates to a new and improved method for environmentally stress screening products by subjecting the products to thermal and vibrational stimuli, optimally simultaneously. Other stresses such as electric power cycling, voltage changes, and input power frequency variations may be introduced to the products being screened, and the products can be monitored to determine if the products function and continue to function as expected. It has been found that these combined thermal and vibrational stimuli, when combined with simultaneous rigorous functional monitoring, enable root cause corrective action to be implemented to remedy the cause of latent defects uncovered during the screening. Environmental screening in accordance with the present invention can lead to significant product quality improvements, production cost reductions, reduced warranty repair expense, increased customer satisfaction, and increased market share.

Applications of the current state of the art in environmental screening is very energy, time, and effort intensive, thereby rendering such screening very expensive. Existing screening techniques utilize temperature cycling within a chamber which, in more advanced cases, also has a product vibrating device within it. The chamber itself and the vibrating device act as thermal loads on the chamber, thus requiring more energy to heat and cool the electronic product being tested through the desired thermal cycles. Both the vibrating device and the thermal loads react to temperature changes, radiating and/or absorbing thermal energy in response to changes in ambient temperature. Accordingly, changing the temperature of the chamber and the vibrating device naturally requires more energy than if just the product were to be cycled through temperature changes. In some cases, the chamber and vibrating device consume the majority of the energy costs to no useful end. Additionally, cycling the chamber and vibrating device through various temperature changes requires more time than if just the product were to be cycled.

As an alternative to screening products by cycling them through different temperatures in a single, variable-temperature chamber, products may be successively moved into and subjected to multiple temperature-controlled chambers which are maintained at different fixed temperatures. Existing "thermal shock chambers" shuttle products between temperature-controlled chambers to subject the products to differing extremes of temperature. However, when the chambers are opened or closed to insert and remove products being screened, thermal energy can be exchanged with adjacent chambers and/or the ambient environment, and energy will be wastefully consumed in restoring the desired temperature within the chambers. Further, manual intervention is required if the products to be screened must be connected to or disconnected from vibrating devices or other testing devices, and additional thermal energy will be lost to the ambient environment while the chambers are open to allow the connections to be made.

Where screening for defects susceptible to vibration is desirable, energy efficiency concerns are magnified. If a temperature-controlled chamber is equipped with a vibrating device, such as a shaker table, when the chamber is heated and/or cooled, the vibrating device must also be heated or cooled. Accordingly, reaching and/or restoring the desired temperature in the chamber requires additional energy to heat and/or cool the vibrating device, as described above. Further, repeated heating or cooling of the screening apparatus may have detrimental effects on the reliability of the vibrating device due to material fatigue as well as potentially nonuniform thermal expansion and contraction of parts and other effects, which may be detrimental to the operability of moving parts.

In sum, existing environmental screening systems consume energy and time inefficiently. Existing systems also require manual intervention to connect products to testing devices for testing vibrational and other stimuli. It is because of these and other background considerations that the present invention has evolved.

SUMMARY OF THE INVENTION

General objectives of the present invention are to facilitate and enhance environmental screening of products under predetermined testing conditions, to provide more comprehensive screening and to make environmental screening more efficient by reducing the energy, time, and manual intervention required to undertake environmental screening.

One aspect of the present invention is to allow products to be more comprehensively screened under multiple environmental stimuli including temperature changes, vibration, and other stresses. In accordance with this aspect of the present invention, the apparatus and method of the present invention allow products to be simultaneously screened under thermal and vibrational stresses. Moreover, the present invention isolates the source of the thermal stimuli from the source of the vibrational stimuli to minimize the energy wasted in heating or cooling items not being tested.

In accordance with other aspects of the present invention, multiple screening environments are maintained at differing temperatures to subject products to differing extremes of temperature without heating or cooling the entire screening apparatus to test products at different temperatures. Further, products can be moved between screening compartments with little or no manual intervention so that the products can be cost-effectively exposed to rapid changes in temperature. The present invention also allows for connections of the products to be made to vibrating devices and/or other testing devices, such as electronic testing devices, without manual intervention to allow the products to be screened efficiently under vibrational and other stimuli.

A more complete appreciation of the present invention and its scope can be obtained from understanding the accompanying drawings, which are briefly summarized below, the following detailed description of a presently preferred embodiment of the invention, and the appended claims.

DETAILED DESCRIPTION OF THE PREFERRED EMBODIMENT

Figure 1:
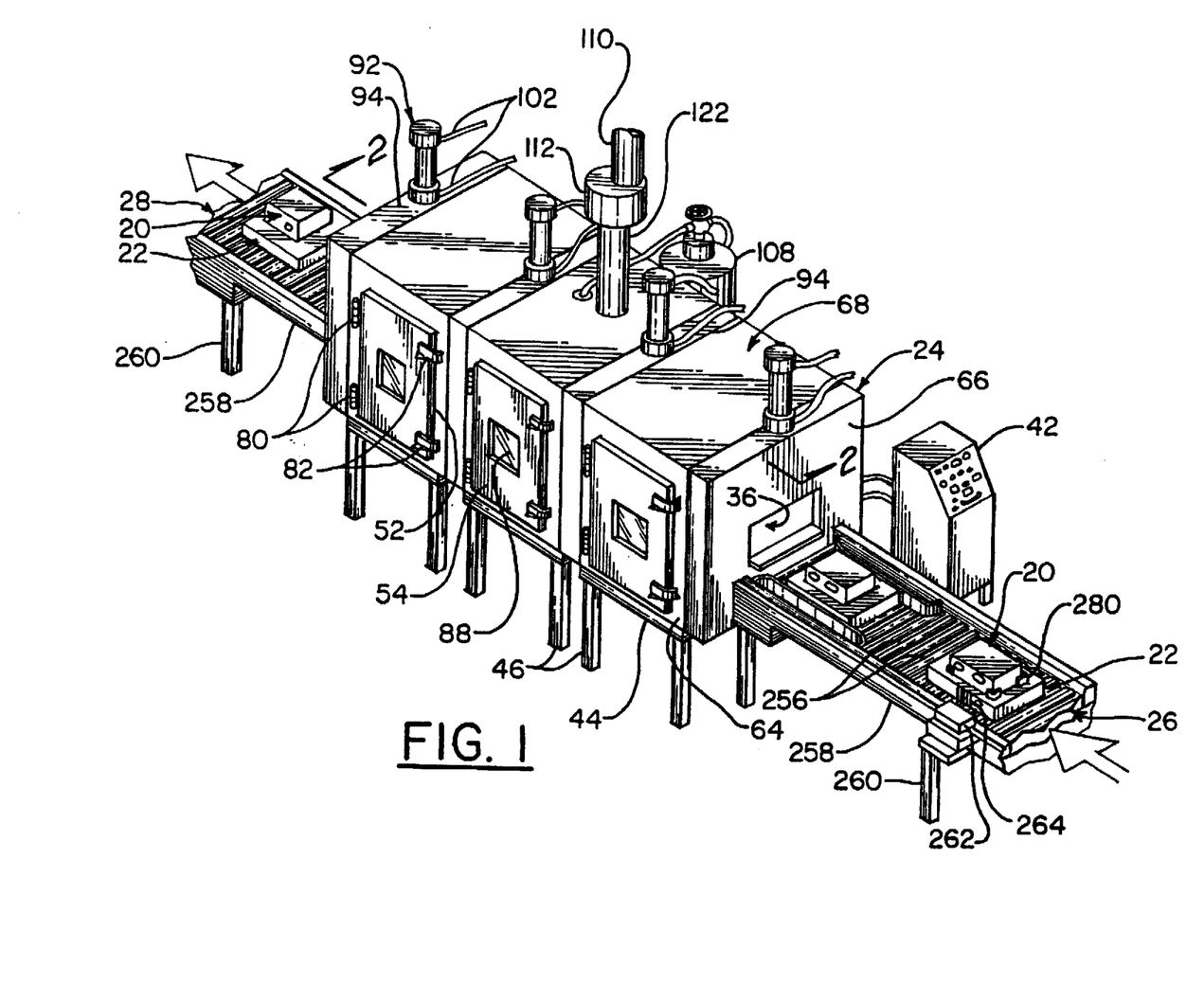
FIG. 1 is an isometric view of the screening apparatus of the present invention.
Figure 2:
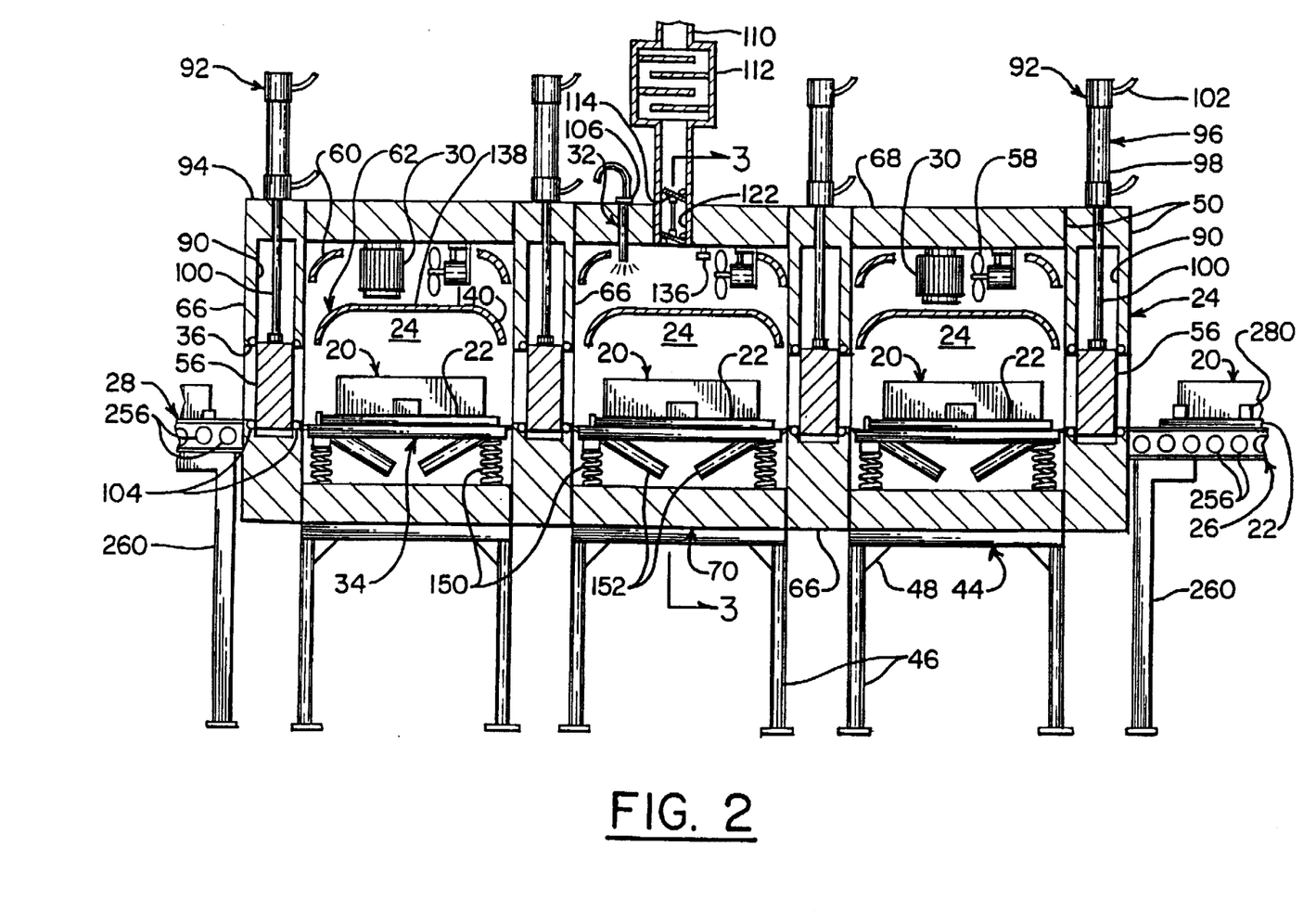
FIG. 2 is a vertical fragmentary section taken along line 2—2 of FIG. 1 showing the interior of the divided screening compartments of the apparatus of the present invention.
Figure 6:
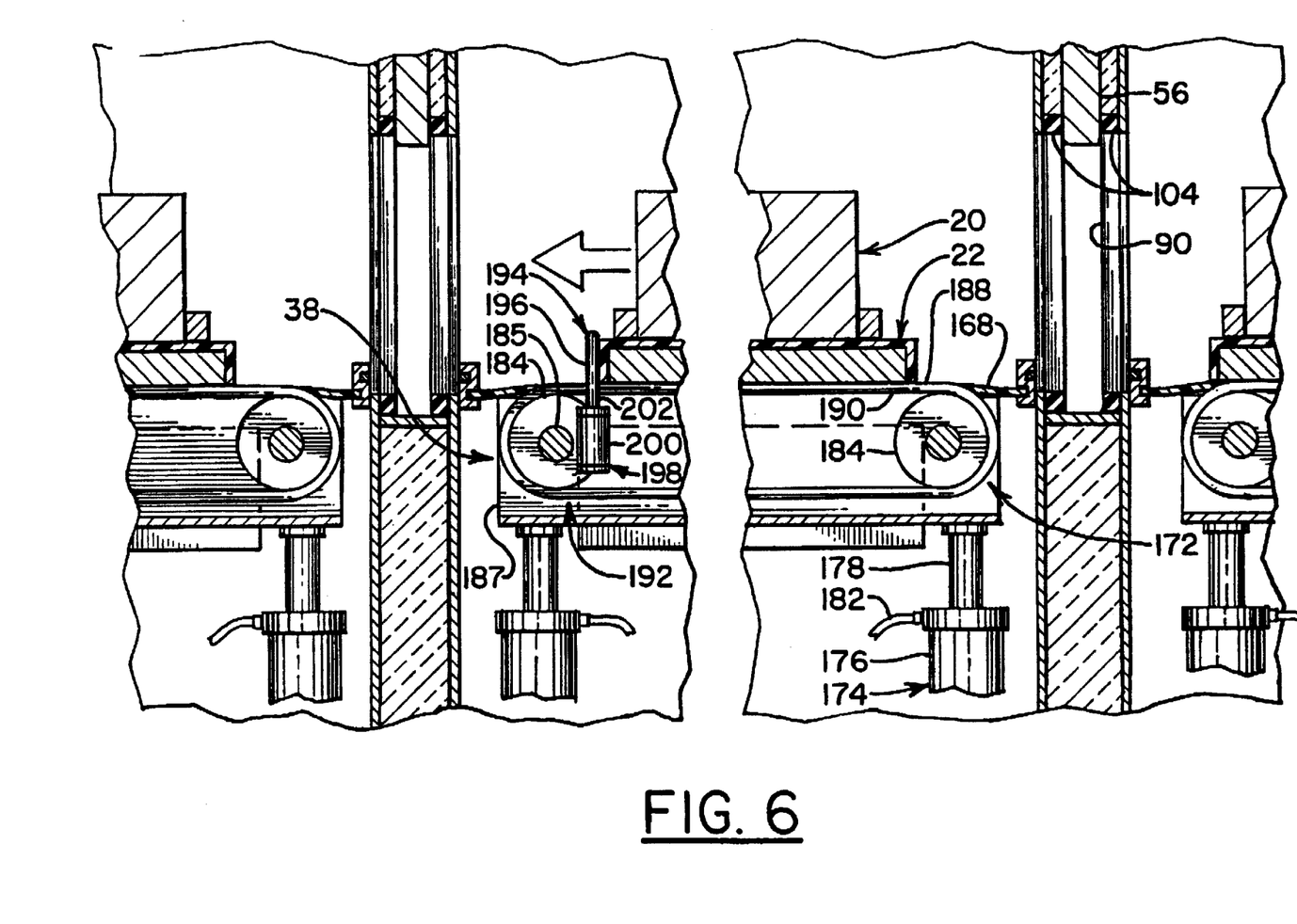
FIG. 6 is an enlarged fragmentary vertical section taken along line 6—6 of FIG. 4 showing the transfer mechanism of the apparatus of the present invention.

The present invention is intended primarily for use for environmentally stress screening products 20 to detect latent defects in the product that can become apparent in vibrational and varying thermal environments. In the apparatus of the present invention, as best seen in FIGS. 1 and 2, products 20 to be screened are mounted on specially-designed pallets 22, which are moved into the first of a series of divided screening chambers or compartments 24 by an entry conveyor 26 and removed from the series of chambers 24 by an exit conveyor 28. The divided screening compartments 24 are each equipped with a heating device 30, as shown in the first and last chambers 24 in FIG. 2, and/or a cooling device 32, as shown in the middle chamber 24 in FIG. 2, and an insulated vibrating device 34. Since each of the compartments 24 are substantially the same as the others, the same numerals will be considered to refer to similar components in each of the compartments 24 unless otherwise designated. Products 20 are transferred into and out of each of the divided screening compartments 24 through transfer doorways 36 by transfer mechanisms 38, as best seen in FIG. 6 and which will be described in more detail below. Automated actuator arms 40, as shown in FIGS. 3, 4, and 9–12, permit electrical connections to be established with the products 20 during screening so that the products 20 can be put through electrical test procedures concurrent with the vibration and thermal stresses applied by the apparatus of this invention. The system is controlled from an operation console 42.

Referring again to FIGS. 1 and 2, the screening system of the present invention comprises a series of individual divided screening compartments 24, each of which is supported by a platform 44 having a number of interconnected supporting legs 46 and braces 48. As shown in FIG. 2, the compartments 24 comprise a plurality of insulated walls 50, which isolate each divided screening compartment 24 from the ambient environment and from adjacent compartments 24. Each individual divided screening compartment 24 is accessible by a user through access doorways 52 in the lateral sides 50 of each compartment 24, which doorways 52 can be selectively closed and sealed with access doors 54 (FIG. 1). The compartments 24 are also equipped with the transfer doorways 36 which interconnect the interiors of the adjacent compartments 24 with each other and with the ambient environment in a manner that accommodates movement of the products 20 sequentially into and out of adjacent chambers 24. The transfer doorways 36 are selectively opened or closed and sealed by vertically sliding doors 56, as best seen in FIG. 2.

Each compartment 24 can be equipped with temperature control apparatus, such as a heating device 30, as shown in the first and last compartment 24 in FIG. 2, and/or a cooling device 32, as shown in the middle chamber 24 of FIG. 2. Each chamber 24 can also have a circulating fan 58, corner baffles 60, and a channelling baffle 62 to control the exchange of thermal energy with the products 20 that are being screened. Each compartment 24 also includes a vibrating device 34 to expose products 20 to vibrational stresses. The transfer mechanism 38, shown in FIGS. 3–6 and described in more detail below, in each of the compartments 24 transfers products 20 into and out of each chamber or compartment 24. The actuator arm 40, shown in FIGS. 3–5 and 9–12 and described in more detail below, allows the product 20 to be connected electrically with an electronic function testing device (not shown) while the product 20 is positioned in a compartment 24, as will also be further described below.

Figure 3:
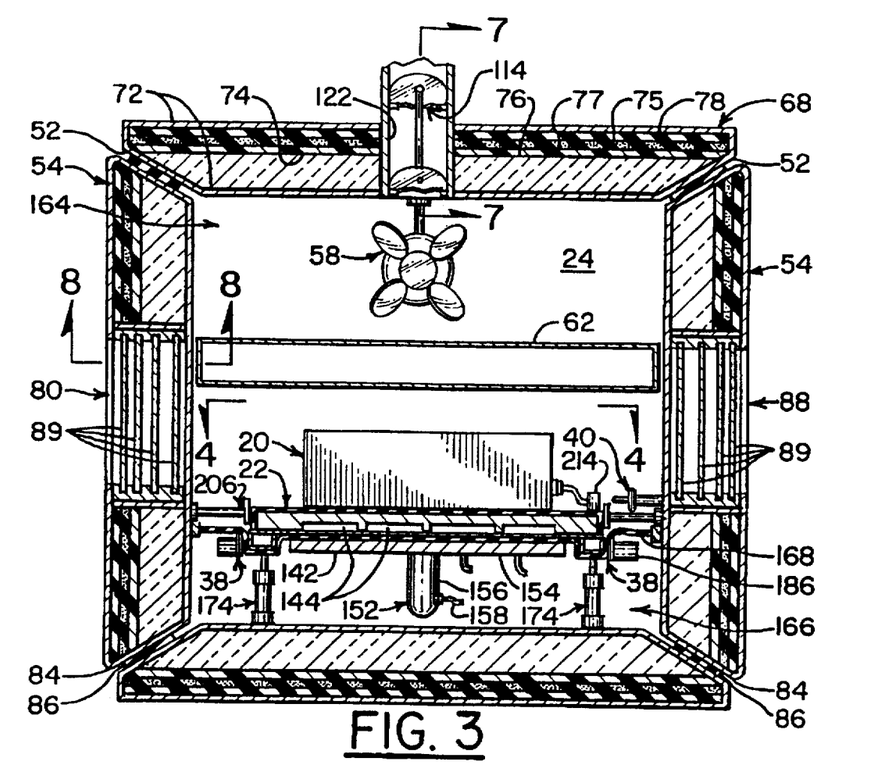
FIG. 3 is an enlarged vertical fragmentary section taken along line 3—3 of FIG. 2 showing the inside of a single divided screening compartment of the apparatus of the present invention.

As shown in FIGS. 1, 2, and 3, the insulated walls 50 of the divided screening compartments 24 include lateral side walls 64 (FIG. 1), transverse side walls 66, an upper wall 68 and a lower wall 70, each of which are comprised of a shell 72 of a rigid structural material surrounding a core 74 of insulating material. The shell 72 in the preferred embodiment is made of stainless steel, which is durable, resists corrosion and is easy to clean. The insulating core 74 is comprised of materials resistant to conduction of thermal energy, and consequently the core 74 resists transmission of thermal energy between adjacent chambers or compartments 24 and/or the outside environment. The insulating material 74 also resists transmission of acoustic waves so that noise generated within the compartments is insulated from the ambient environment. The core 74 includes an inner layer 76 preferably of fiberglass, which provides thermal insulation as well as some degree of acoustic insulation, and an outer layer 78 preferable of a visco-elastic damping material, which provides additional acoustic insulation by damping vibration of the outermost layer of the shell 72. A suitable visco-elastic material is manufactured by Kinetics West, 7059 South Curtice Street, Littleton, Colo. 80120, under the product name "AAP Damping Sheets with ¼ inch foam and No. 1 barrier." This multi-layered thermal and acoustic insulation/barrier 74 is presently used in screening chambers manufactured by the QualMark Company, 1343 West 121st Avenue, Denver, Colo. 80234, marketed under model numbers OSV-1, OSV-2, OSV-3 and OSV-4.

Both lateral side walls 64 of the divided screening compartments 24 include manual access doorways 52 which are fitted with the manual access doors 54 to selectively open or close and seal the compartments 24. The manual access doorways 52 allow manual access to the interior of the compartments 24 and facilitate construction and maintenance of the compartments 24 (FIGS. 1 and 3). The manual access doors 54 have the same structure as the compartment walls 50, comprising a shell 72 of rigid structural material surrounding a core 74 of insulating/barrier/damping material 76 and 78. The access doors 54 are mounted to the lateral side walls 64 of the compartments 24 with hinges 80 and are secured in a closed position by releasable latches 82. The edges 84 of the access doors 54 are fitted with seals 86 (FIG. 3) to secure the isolation of each compartment 24 from the ambient environment.

Figure 8:
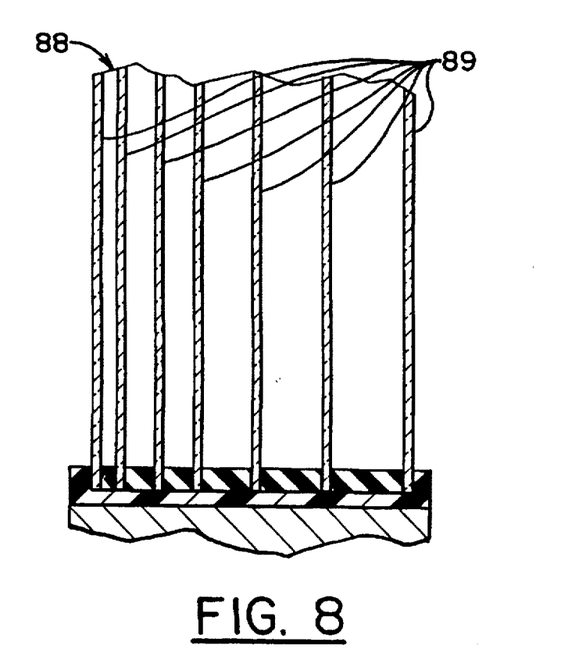
FIG. 8 is an enlarged fragmentary vertical section of the viewing window taken along line 8—8 of FIG. 3.

Each access door 54 is fitted with a transparent viewing window 88 to allow visual monitoring of the compartment 24 from outside. In the preferred embodiment, each window 88 comprises multiple panes 89, as best seen in FIGS. 3 and 8. The multi-pane windows 88 have unequal spacing between panes 89 so as to stop certain discrete frequencies of sound from propagating through the multi-pane windows 88 via standing waves, whereas propagation of waves of such frequencies would be possible if the spaces between each of the panes 89 were equal (FIG. 8). Particularly, in the preferred embodiment, seven panes 89 are used, spaced at intervals relative to a base unit of measure at a relative spacing of 1.0, 1.1, 1.2, 1.3, 1.4 and 1.5 units, commencing from either the innermost or outermost pane. By using unequal interpane spaces, standing waves are avoided and better overall reduction in sound transmission results.

Transfer doorways 36 are formed in each of the transverse side walls 66 of each compartment 24 with the doorways 36 being selectively openable or closeable and sealable with the sliding doors 56 as best shown in FIGS. 2 and 6. The sliding doors 56 are formed similarly to the walls 64, 66, 68, 70 of the compartments 24 and the access doors 54, comprising a shell 72 of rigid structural material surrounding a core 74 of insulating material. The sliding doors 56 are slidably received in recesses 90 in the transverse side walls 66.

The sliding doors 56 are opened and closed by door actuators 92 (FIGS. 1 and 2) comprising conventional pneumatic lifting devices mounted on an upper edge 94 of each of the transverse side walls 66. The door actuators 92 each include a power cylinder 96 having a cylinder body 98 mounted on the upper edge 94 of the associated transverse side wall. An associated piston rod 100 extends downwardly into the recess 90 of the associated transverse side wall 66 and is operatively connected to a sliding door 56. The power cylinders 96 are actuated by gas pressure supplied through pressure couplings 102, which connect the power cylinders 96 with a gas pressure source (not shown). Reciprocal operation of the power cylinders 96 thereby selectively moves the sliding doors 56 vertically between open and closed positions. The door actuators 92 are controlled from the operation console 42.

The transfer doorways 36 are fired with a pair of peripheral door seals 104, shown in FIG. 6, which extend around opposing faces of each transfer doorway 36. The seals 104 are hollow and are inflatable with pressurized gas when the doors 56 are in the closed position, the gas pressure being supplied from a gas pressure source (not shown) through pressure couplings (not shown). The gas pressure, of course, causes the seals 104 to expand to securely engage opposite sides of the sliding door 56 to hermetically seal the associated compartment 24, thereby ensuring the integrity of the insulation between adjacent compartments 24 and the ambient environment. Correspondingly, the seals 104 can be deflated by releasing the gas pressure from the seals 104, thereby loosening the engagement of the seals 104 against the sliding doors 56 to allow the sliding doors 56 to be moved more freely.

Each compartment 24 incorporates a heating device 30 or a cooling device 32, as shown in FIG. 2. These devices 30 or 32 heat or cool the atmosphere of each compartment 24 by exchanging thermal energy with whatever gas is in the chamber 24. In the preferred embodiment, the heating devices 30 are heating coils and are mounted on the upper walls 68 of the outermost compartments 24. The heating coils of device 30 are of a known type comprising electro-resistive coils which generate heat when electrical current is circulated through them. The heating devices 30 are controlled in a conventional manner from the operation console 42. The cooling device 32 in the preferred embodiment is mounted on the upper wall 68 of the center compartment 24 and comprises an input valve 106 adapted to selectively introduce a low-boiling point fluid, such as liquid nitrogen, directly into the compartment 24. The liquid nitrogen can be supplied from a conventional pressurized canister 108 (FIG. 1) suspended from one lateral side 66 of a screening compartment 24. The input valve 106 is also controlled in a conventional manner from the operation console 42. Liquid nitrogen introduced into the compartment 24 boils or flashes immediately into its gaseous state. The boiling of the liquid nitrogen absorbs heat of vaporization from the atmosphere of the compartment 24 and from the product 20 in the compartment 24. Beneficially, the boiling and expansion of the nitrogen also displaces any moisture which may have accumulated on the surface of the product 20 in the compartment 24. However, because the transition of the liquid nitrogen from its liquid to gaseous state involves a tremendous expansion in volume, an exhaust pipe 110 is provided through the upper wall 68 of the center compartment 24 to allow the release of the gas pressure as necessary. In order to minimize the noise attending the expansion and release of the nitrogen from the center compartment 24, as well as noise emanating from the vibrating device 34 within the chamber 24, a multi-baffled muffler 112 is fitted to the exhaust pipe 110.

The release of gas pressure through the exhaust pipe 110 is controlled by a one-way flapper valve 114, which allows gas to pass only from the compartment 24, not into the compartment 24. If the gas pressure within the compartment 24 were to drop below the atmospheric pressure of the ambient environment and gas were permitted to flow from the ambient environment into the compartment 24, which has been cooled by the introduction of the low boiling point fluid, moisture inherent in the ambient environment would flow into the chamber 24, potentially resulting in condensation and freezing of the moisture within the compartment 24. Build-up of such condensation and/or freezing of the moisture within the chamber or compartment 24 could negatively impact the product 20 being tested and various devices within the compartment 24, thereby hampering screening and potentially damaging the product 20.

Figure 7:
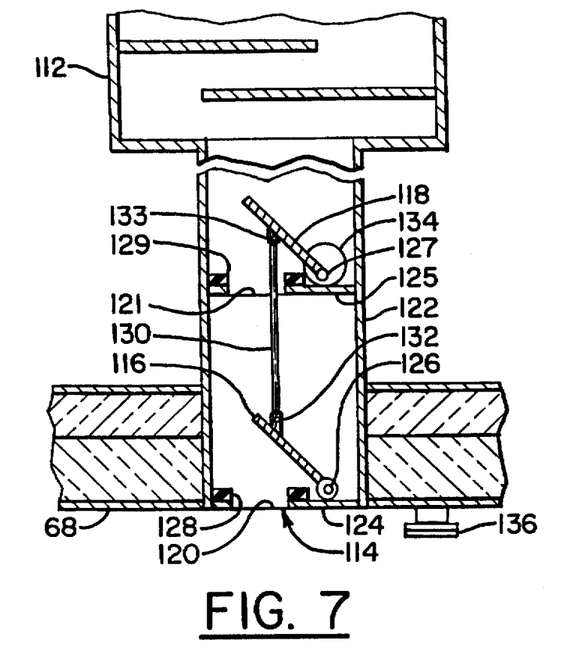
FIG. 7 is an enlarged fragmentary vertical section of the valve chamber taken along line 7—7 of FIG. 3.

The flapper valve 114, best shown in FIG. 7, includes a lower cover piece 116 and an upper cover piece 118 which are fitted to close two spaced apart openings 120, 121 in a valve chamber 122 of the exhaust pipe 110. Each cover piece 116, 118 is secured to horizontal dividing walls 124, 125 within the valve chamber 122 at one end by respective hinges 126, 127. Each of the openings 120, 121 in the valve chamber 122 is fitted with a gasket 128, 129, respectively, to securely seal the openings 120, 121 in the valve chamber 122 when the cover pieces 116, 118 are in a closed position. The cover pieces 116, 118 are connected by a rigid coupling rod 130 joining respective pivotal joints 132, 133 on the upper surface of the lower cover piece 116 and the underside of the upper cover piece 118, the coupling rod 130 ensuring movement of the cover pieces 116, 118 in unison with each other. The opening and closing of the upper cover piece 118 is controlled by a servo-motor 134 controlled from the operation console 42 (FIG. 1). The opening and closing of both cover pieces 116, 118 thus can be selectively controlled in response to the gas pressure measured within the chamber 24 by a pressure transducer 136 mounted within the chamber 24, as shown in FIG. 7, to maintain the gas pressure within the compartment 24 close to the atmospheric pressure of the ambient environment to prevent gas from flowing back into the compartment 24. The opening and closing of the cover pieces 116, 118 can be conventionally automatically controlled in response to the level of gas pressure in the chamber 24 measured by the pressure transducer 136.

When using a plurality of divided screening compartments 24 in sequence, it is important to note that the last compartment 24 positioned before the exit conveyor 28 (FIGS. 1 and 2) should preferable employ a heating device 30 and thereby be a hot chamber. If the last compartment 24 were a cold compartment, potentially undesirable condensation could form on the products 20 once the products 20 are returned to the ambient environment.

Cooling and heating within the compartments 24 are controlled and enhanced by the circulating fans 58 (FIGS. 2 and 3). Circulating the gas within the compartments 24 accelerates heating or cooling of the gas within the compartment 24 by increasing contact between the gas and the heating device 30 or the cooling device 32. Similarly, circulation of the gas in the compartments 24 enhances the imparting or absorbing of thermal energy between the gas and the product 20 in a compartment 24. The rate of transfer of thermal energy to the products 20 in the compartments 24 can be controlled by regulating the speed of the circulating fans 58, as well as controlling the amount of heating and cooling emanating from the respective devices 30, 32, as described above. The circulating fans 58 are controlled from the operation console 42.

Circulation of the gas in the compartments 24 is also enhanced by corner baffles 60 and channeling baffles 62 (FIG. 2) within each compartment 24, which optimally direct the flow of gas within the compartment 24. Both the corner baffles 60 and channeling baffles 62 preferably extend the full interior width of each compartment 24. The curved corner baffles 60 mounted in upper corners of each compartment 24 reduce the turbulence and fluid friction of the flow of gas within each compartment 24, which otherwise would be restricted by the opposing surfaces of the walls of the compartment 24 meeting at a corner. The channeling baffles 62 suspended from the upper walls 68 of the compartments 24 by baffle supports (not shown) similarly enhance the circulation of gas. Each of the channeling baffles 62 has a flat mid-portion 138 terminating with curved edge portions 140. The flat mid-portion of the channeling baffle 62 aids in directing the gas in the compartment 24 in a cyclical flow driven by the circulating fan 58. The curved edge portions 140 of the channeling baffles 62 preferably have approximately the same curvature as the corner baffles 60 in the plane of the lateral side walls 64 in order to facilitate a smooth, cyclical flow of gas around the interior of each compartment 24.

Figure 5:
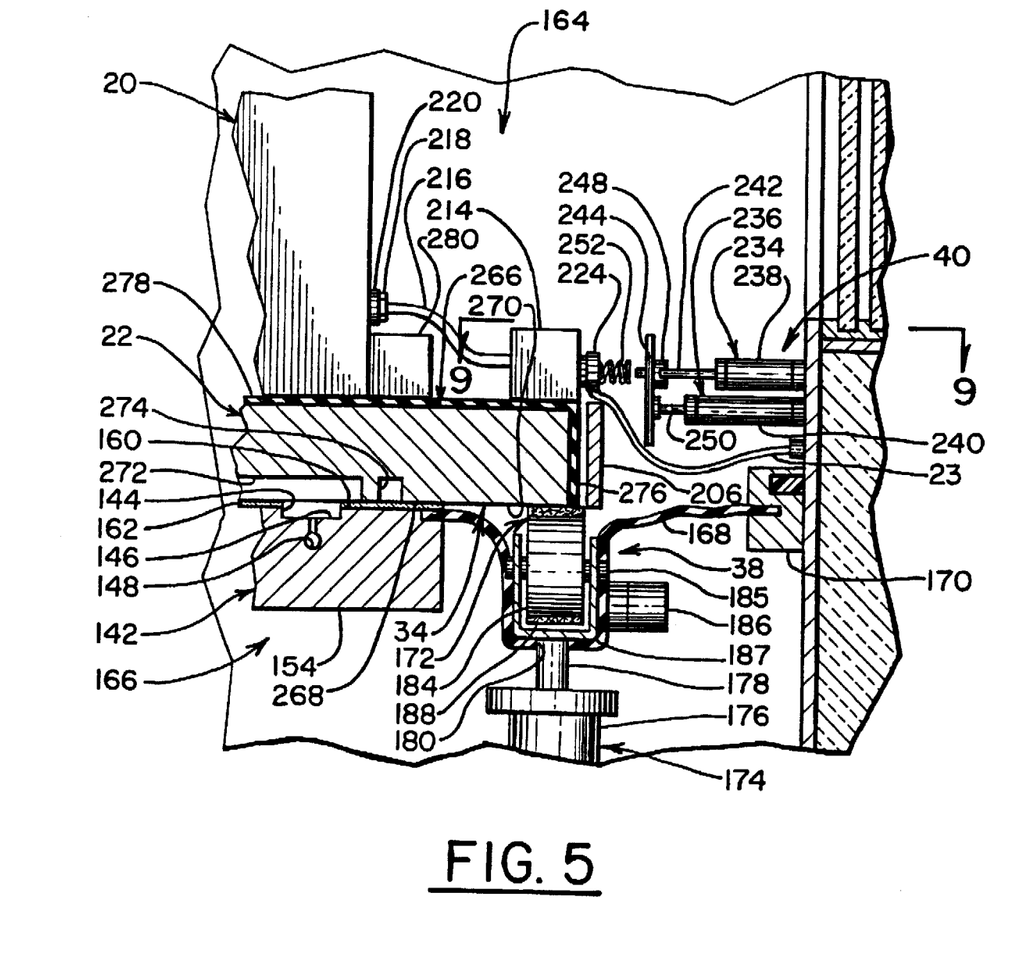
FIG. 5 is an enlarged fragmentary vertical section taken along line 5—5 of FIG. 4 showing a portion of the vibrating device and transfer mechanism of the apparatus of the present invention.

Each compartment 24 also incorporates a vibrating device or shaker table 34, as best seen in FIGS. 2, 3, and 5. The vibrating device 34 optionally is used to impart vibration to the product 20 being screened. As shown in FIG. 5, the vibrating device 34 includes a mounting platform 142, which supports a pallet 22 that in turn holds the product 20 being screened. In the preferred embodiment, the mounting platform 142 is hollow and includes a plurality of vacuum ports 144, which assist in securing the pallet 22 to the mounting platform 142 by vacuum pressure applied through the vacuum ports 144. The mounting platform 142 of the vibrating device 34 has a hollow interior 146 (FIG. 5) in communication with the vacuum ports 144 and a source of vacuum (not shown) connected to the vacuum ports 144 through pressure couplings 148. The operation of the vacuum ports 144 is controlled at the operation console 42.

The mounting platform 142 is generally supported from the lower wall 70 of each compartment 24 by a plurality of resilient support elements 150 (FIG. 2). These resilient support elements 150, comprising springs in the preferred embodiment, support the weight of the mounting platform 142, the pallet 42, and any product 20 mounted thereto, but do not impede the vibration generated by the vibrating device 34.

Vibration is generated by a plurality of exciters 152 (FIG. 2) rigidly attached to the underside 154 (FIG. 5) of the mounting platform 142. The exciters 152, shown in FIGS. 2 and 3, in the preferred embodiment are conventional pneumatic vibrators. The pneumatic vibrators 152 incorporate an enclosed cylinder housing 156, a free floating piston (not shown) therein and pressure couplings 158 connecting the cylinder 156 with a source of gas pressure (not shown). The repeated collisions of the free piston (not shown) with the cylinder housing 156 impart shock pulses to the cylinder housing 156, thereby imparting vibration to the cylinder housing 156 and to the platform structure 142 connected thereto. In this case, the vibrations are imparted to the mounting platform 142 and, in turn, to the pallet 22 and the product 20 positioned on the platform 142. The amount of vibration can be controlled by regulating the gas pressure supplied to the exciter 152 from the gas pressure source. Multiple exciters 152 can be employed to impart vibrations to the mounting platform 142 in one or more axes to provide universal vibrational motion to the product 20. Vibrating devices or exciters 152 of the type mounted in screening chambers marketed by the QualMark Company (reference above) under model numbers OSV-1, OSV-2, OSV-3 and OSV-4 have been found suitable for this apparatus, although a variety of suitable exciters are available from numerous manufacturers as is well-known to persons skilled in this art.

In screening the products 20, it is not necessary to heat and cool the vibrating device 34. Accordingly, the upper surface 160 of the mounting platform 142 can be covered with an insulating layer 162 (FIG. 5), which limits the exchange of thermal energy between the mounting platform 142 and the gas in the compartment 24 as well as between the mounting platform 142 and the pallet 22. In the preferred embodiment, the insulating layer 162 is comprised of a fluorosilicon rubber, which not only restricts the exchange of thermal energy between the mounting platform 142 and the pallet 22 mounted thereon, but also provides a slip-resistant surface to aid in maintaining positioning of the pallet 22 on the mounting platform 142. The insulating layer 162 does not cover the vacuum ports 144.

Moreover, to insulate the support elements 150 and exciters 152, each compartment 24 is divided into a testing chamber 164 and a control chamber 166 by an elastic boot or diaphragm 168 (FIG. 3 and 5), which extends between and joins the mounting platform 142 to the lateral side walls 64 and transverse side walls 66 of each compartment 24. The diaphragm 168 is joined to the walls 64, 66 by a molding strip 170 (FIG. 5). The diaphragm 168 prevents gas from flowing from the testing chamber 164 into the control chamber 166, thereby insulating the support elements 150 and exciters 152 (FIG. 2) from the testing chamber 164. However, the diaphragms 168 are sufficiently resilient so as not to dampen the vibration imparted by the vibrating device 34. Accordingly, the diaphragm 168 minimizes the waste of energy in heating and/or cooling the vibrating device 34. Furthermore, because the diaphragm 168 prevents gas from flowing from the testing chamber 164 into the control chamber 166, the diaphragm 168 aids in maintaining the cyclical circulation of the gas in the testing chamber 164 as facilitated by the corner baffles 60 and channelling baffles 62.

Each compartment 24 also includes a transfer mechanism 38, as best shown in FIG. 6. Once a screening cycle has been completed in a compartment 24, the transfer mechanism 38 transports the pallet 22 on which the product 20 is mounted into the next compartment 24 or onto the exit conveyor 28 (FIGS. 1 and 2). Specifically, the transfer mechanism 38 in the preferred embodiment comprises pairs of rolling devices in the nature of endless-belt type conveyors or tractors 172 (FIG. 4, 5, and 6), which are retractably-mounted for vertical reciprocative movement adjacent opposite lateral sides of the mounting platform 142 and beneath opposite sides of the pallet 22 disposed on the mounting platform 142, but above the diaphragm 168. The tractors 172 are supported by pairs of extendable pneumatic power cylinders 174, one power cylinder 174 at each end of a tractor 172, and each power cylinder 174, comprising a cylinder body 176 and an extendable piston rod 178. The cylinder bodies 176 are mounted on the lower wall 70 of each compartment 24, and the piston rods 178 sealingly extend through openings 180 in the diaphragm 168 (FIG. 5) for connection to the tractors 172. The power cylinders 174 are operated through a gas pressure source (not shown) connected to the power cylinders 174 through pressure couplings 182. The tractors 172 are deployed by extending the piston rods 178 in unison and thereby raising the tractors 172, causing the tractors 172 to engage the undersurface of an aligned pallet 22, as shown in FIG. 5, and lift the pallet 22 with the product 20 supported on the pallet 22 from the mounting platform 142.

As best seen in FIGS. 5 and 6, each of the tractors 172 comprises a pair of pulleys 184 rotatably mounted on a shaft 185 supported in a frame 187. One of the pulleys 184 is driven by a motor 186 (FIG. 5), while the other pulley 184 is passively rotatable. The pulleys 184 support an endless belt 188 whose underside 190 engages the outer surfaces 192 of the pulleys 184. When the tractor 172 is activated, the motor 186 rotates the associated pulley 184, causing the endless belt 188 to rotate around the pulleys 184. Thus, once the tractors 172 are extendably deployed or raised to engage a pallet 22, the endless belts 188 engage the undersurface of the pallet 22, and the rotation of the endless belts 188 roll the pallet 22 toward its next destination, either to the next compartment 24 or to the exit conveyor 28 (FIGS. 1 and 2).

Figure 4:
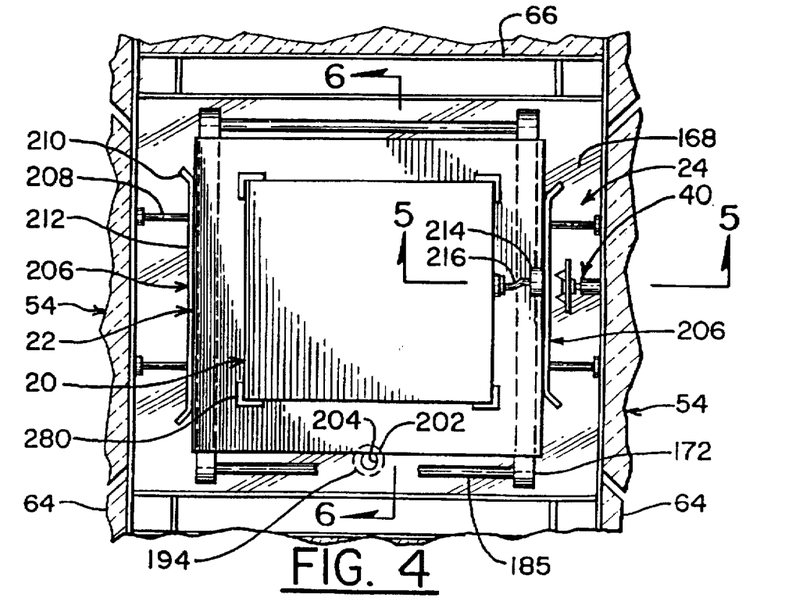
FIG. 4 is a horizontal fragmentary section taken along line 4—4 of FIG. 3 showing the inside of a single testing chamber.

Forward movement of the pallets 22 is controlled by pneumatically retractable stops 194 as best seen in FIGS. 4 and 6 positioned between the forward ends of the left and right tractors 192. The stops 194 each comprise a stop prong 196 mounted atop a pneumatic power cylinder 198. The cylinder 198, as best seen in FIG. 6, includes a cylinder body 200 and an extendable piston rod 202. The cylinder body is vertically mounted on the mounting platform 142. The power cylinder 198 is operated through gas pressure provided by a gas pressure source (not shown) through pressure couplings (not shown). The power cylinder 198 causes the piston rod 202, which sealingly extends through a stop opening 204 in the diaphragm 168, to extend the stop prong 196 upwardly to engage the pallets 22 when they are being moved by the tractors 172. The stops 194 are controlled from the operation console 42, and they engage the pallets 22 to inhibit and selectively stop forward translational movement of the pallets 22. An electrical sensor (not shown) may be fitted on the stop prong 196 to generate a signal to the operation console 40 that the pallet 22 has contacted the prong 196, and the tractors 172 are then deactivated.

The motion of the pallets 22 is also governed by guide rails 206, which position the pallets 22 in the compartments 24, as shown in FIG. 4. There are two guide rails 206 in each compartment 24, one on each side of the path to be followed by the pallets 22 as they move through the compartment 24. The guide rails 206 are mounted on support braces 208 secured to the inside surfaces of the access doors 54, the access doors defining part of the lateral side wall 64 of each compartment 24, as described above. The guide rails 206 are mounted at a predetermined height above the plane of the mounting platform 142 as shown in FIG. 5. They are spaced from each other a distance slightly greater than the width of a pallet 22 to help guide the pallet 22 into and out of the associated compartment 24 while allowing for vibrational movement of the pallet 22 such as imposed by a vibrating device 34 (FIG. 2). Each guide rail 206 has oblique end portions 210 flared outwardly from a straight center portion 212, as best seen in FIG. 4. The oblique end portions 210 present a flared opening between the guide rails 206 juxtaposed on opposite sides of compartment 24, which receives the pallets 22 as they are transported into the compartment 24. The oblique end portions 210 channel the pallets 22 into the center of the compartment 24, if necessary, where the pallets 22 are guided into place by the straight center portions 212 of the guide rails 206, facilitating controlled positioning of the pallets 22.

Figures 9, 10:
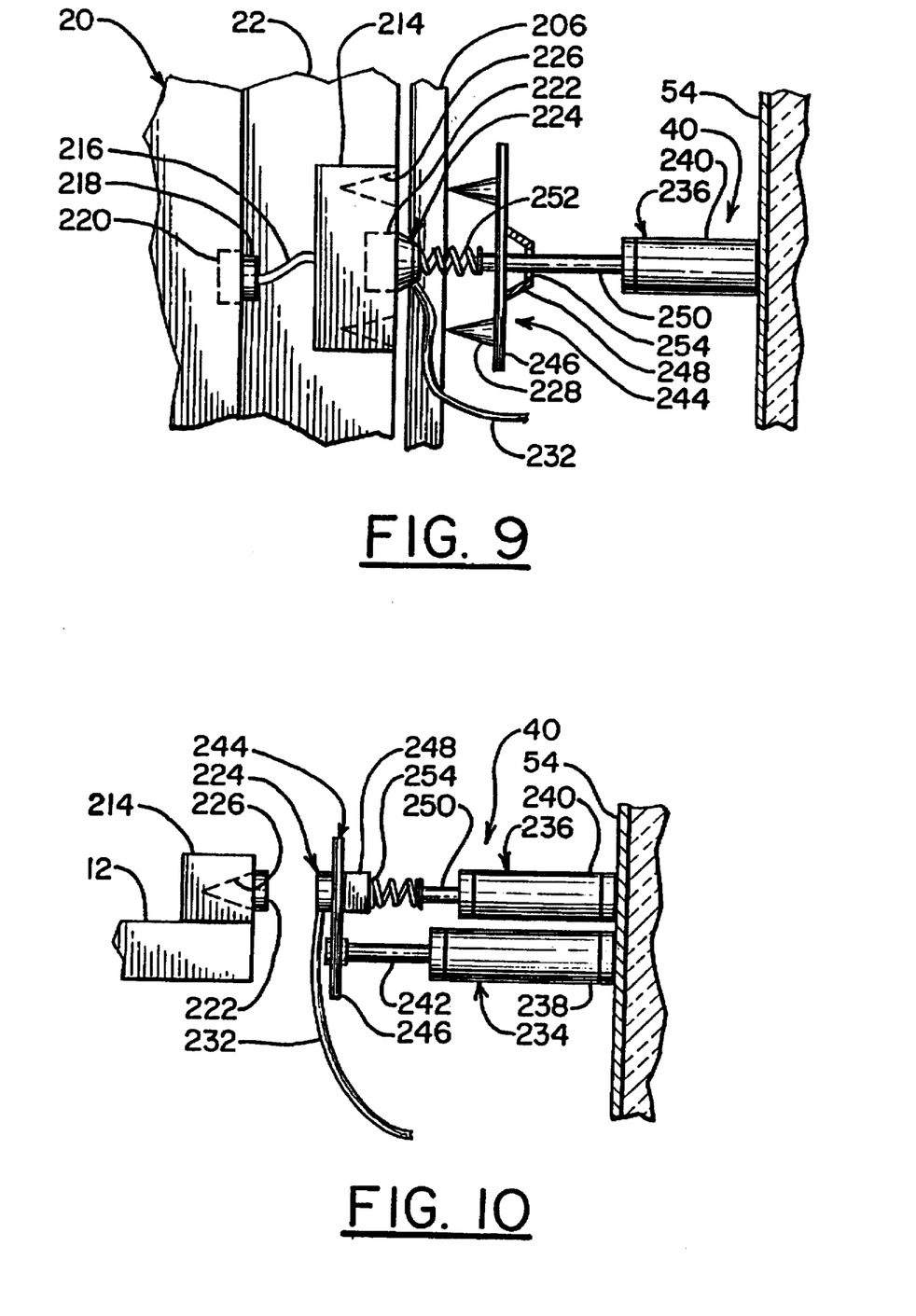
FIG. 9 is an enlarged fragmentary vertical section of the actuator arm taken along line 9—9 of FIG. 5.
FIG. 10 is an enlarged fragmentary side view of the actuator arm shown in FIG. 5 in a retracted condition.
Figure 11:
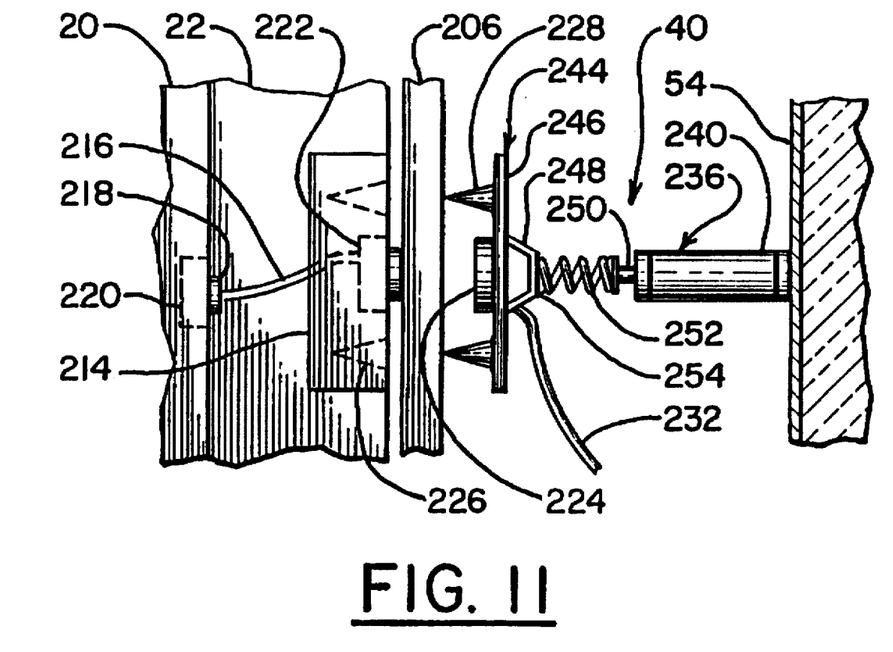
FIG. 11 is an enlarged fragmentary plan view of the actuator arm shown in FIG. 5.

The controlled positioning of the pallets 22, as described above, facilitates comprehensive screening by electrical testing devices (not shown) of products 20, including electrical components. Each of the pallets 22 can be fitted with an electrical receptacle 214, as shown in FIGS. 5, 9, and 11, which receives one end of a set of electrical connectors 216. At the other end of the connectors are plugs 218 (FIG. 5), which are matched to electrical sockets 220 (FIG. 5) of the type sometimes found on products 20. The connectors 216 permit electrical communications to be established between the product 20 and the receptacle 214, which in turn permits communication with a testing device (not shown) that is a source of electrical communications. Specifically, the connectors 216 allow the exchange of power, control signals, and other electrical transmissions with the product 20 being screened. The plugs 218 are attached to the mating sockets 220 on the product 20 when the product is first mounted on its associated pallet 22 prior to entering the compartments 24.

As shown in FIGS. 9-12, the receptacle 214 has a test plug jack 222 adapted to receive a test plug 224 and two guide pin sockets 226 adapted to receive guide pins 228 for directing the test plug 224 into place. The test plug 224 has a tapered back end 230 used for orienting the test plug as will be explained below. The test plug 224 is connected to a testing device as mentioned above, by flexible conductors 232. The test plug 224 is engaged and disengaged with the receptacle 214 by an actuator arm 40, to which the test plug 224 is permanently attached.

In the preferred embodiment, the actuator arm, generally depicted in FIGS. 3, 4, and 5, and 9-12 as 40, comprises a first horizontally-reciprocating power cylinder 234 (FIGS. 5, 10, and 12) and a second horizontally-reciprocating power cylinder 236 (FIGS. 5 and 9-12). The first cylinder 234 has a cylinder body 238 mounted on the inside of the access door 54. Similarly, the second cylinder has a cylinder body 240 mounted on the inside the an access door 54 mounted directly above the first horizontally-reciprocating cylinder 234. The first cylinder 234 includes an extendable piston rod 242 which supports a test plug guide plate 244. The guide plate 244 includes a base plate 246, which supports a guide plug bracket 248 and the two tapered guide pins 228. The guide plug bracket 248 releasably receives the tapered back portion 230 of the test plug 224 when the test plug 224 is in the retracted position. The back portion 230 of the test plug 224 and the test plug bracket 248 are shaped to ensure that the test plug 224 is properly oriented to engage the receptacle 214 when the actuator arm is deployed to engage the test plug 224 with the receptacle 214. The second power cylinder 236, which is used to remove the test plug 224 from the receptacle 214, includes a piston rod 250 connected to a spring 252, which in turn is connected to the back end 230 of the test plug 224 through an opening 254 in the back of the guide plug bracket 248.

Figure 12:
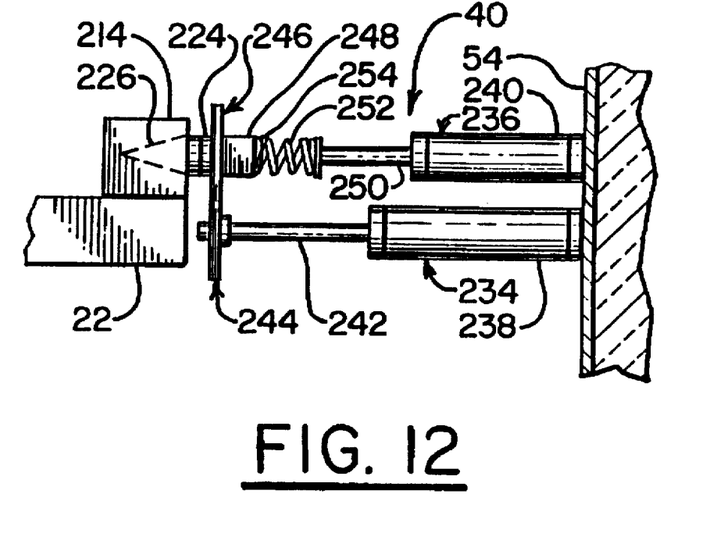
FIG. 12 is an enlarged fragmentary side view of the actuator arm shown in FIG. 5 similar to FIG. 10 with the actuator arm extended.

To engage the test plug 224 with the test plug jack 222 on the receptacle 214, the first power cylinder 234 and second power cylinder 236 are extended simultaneously (FIG. 12). The guide pins 228 on the guide plate 244 are received in the tapered guide pin sockets 226 in the receptacle 214 on the pallet 22, and, as the guide plate 244 is further extended, the tapered pins 228 securely engage the openings 226 to position the test plug 224 over the test plug jack 222 on the receptacle 214. Thus, once the first power cylinder 234 has reached full extension, the guide pins 228 have positioned the test plug 224 to connect with the test plug jack 222 on the receptacle 214, and the test plug 224 is inserted into the jack 222. The first cylinder 234 is then retracted (FIG. 9), withdrawing the guide plate 244 from the receptacle 214, while the second cylinder 236 is left extended. Accordingly, the test plug 224 is left connected to the receptacle 214 on the pallet 22, maintaining electrical communication between the product 20 and the testing device (not shown), and the actuator arm 40 remains flexibly connected with the test plug 224 via the spring 252. Accordingly, once the vibrating device 34 is activated, no rigid members of the actuator arm 40 will impede the vibration imparted by the vibrating device 34.

Once the test phase has been completed and the vibrating device 34 has been deactivated, the first cylinder 234 is re-extended (FIG. 12), the guide pins 228 on the guide plate 244 engaging the guide pin sockets 226 in the receptacle 214, and the test plug bracket 248 receiving the tapered back 230 of the test plug 224. Both the first power cylinder 234 and second power cylinder 236 are then simultaneously retracted, the first cylinder 234 pulling the guide plate 244 away from the receptacle 214, and the second cylinder 236 pulling the test plug 224 out of the jack 222 on the receptacle 214 (FIGS. 10–11). This process is subsequently repeated for successive test phases.

The engagement of the test plug 224 with the receptacle 214 completes the connection between the product 20 being screened and the testing device (not shown). It should be noted that the testing device may subject the product 20 to additional stresses by introducing a range of normal or unanticipated stimuli through power cycling, voltage changes, and input power frequency variations. Such testing devices are known in the art.

The entry conveyor 26 and exit conveyor 28 (FIGS. 1 and 2) allow the pallets 22 to be introduced into and removed from the compartments 24 through the transfer doorways 36. In the preferred embodiment, the entry and exit conveyors 26, 28 are comprised of a number of selectively driven parallel rollers 256, the axes of which extend transversely of the conveyors 26, 28 and lie in a plane parallel with the surfaces of the conveyors 26, 28. The axes of the rollers 256 are also parallel to, and aligned vertically with, the base edge of the transfer doorways 36 at opposite ends of the apparatus. The rollers 256 are rotatably mounted in a conveyor frame 258, which is supported by a number of support legs 260. The rollers 256 permit translational movement of the pallets 22 toward and away from the compartments 24, but they do not permit movement of the pallets 22 along the axes of the rollers transverse to the conveyors 26, 28. In the preferred embodiment, the rollers are selectively powered by motors (not shown) to motivate the pallets 22 toward and away from the series of compartments 24.

The entry conveyor 26 may be equipped with a bar code reader 262 mounted on the conveyor frame 258 at a height even with the pallets 22 when they are positioned on the surface of the entry conveyor 26. Accordingly, the bar code reader 262 is positioned to read bar codes 264 affixed to the pallets 22. The reader 262 may be a passive reader, which reads the code as the bar codes 264 pass by the reader 262, or the reader 262 may be an actively scanning type, which can also read the bar codes 264 when the bar code 264 and the reader 262 are stationary relative to each other. The bar code reader 262 is electrically connected to the operation console 42. In the preferred embodiment, the bar codes 264 are used to encode information concerning the product 20 being screened. The encoded information may include a tracking number for the particular product 20, product type information which corresponds to a predetermined screening sequence stored in the operation console 42, or other pertinent information.

Products 20 to be screened are mounted on specially-designed pallets 22. The pallets 22, as shown in FIGS. 4 and 5, serve as a generalized, transportable platforms for products 20 to be screened. The pallets 22 are primarily composed of rigid, lightweight material. Further, as previously described and shown in FIG. 3, each pallet 22 may be fitted with a receptacle 214 and electrical connectors 216 facilitating electrical interaction with the product 20 to be screened. Each pallet 22 also may bear bar codes 264 identifying the attached product 20.

The pallets 22, which are best seen in FIGS. 4 and 5, have an upper planar surface 266, providing a versatile surface for supporting products 20 to be screened. A lower surface 268 of the pallet has planar edge surfaces 270 which extend beyond the dimensions of the mounting platform 142 and facilitate transport of the pallet 22 by the tractors 172, which are engageable with the lower edge surfaces 268, 270 of a pallet 22 from beneath. Within the dimensions of the mounting platform 142, however, the lower surface 268 of the pallet contains a recess 272, which facilitates the generation of a secure vacuum seal on the pallet 22 by the vacuum ports 144. Structural support of the pallet is buttressed by a number of support standoffs 274 extending from the recess 272, which engage the surface of the mounting platform 142. The positioning of the standoffs 274 does not coincide with the positioning of the vacuum ports 144 so as not to interfere with their operation. Planar side surfaces 276 on the pallets 22 allow the sides to be guided by the guide rails 206 to direct the motion of the pallets 22. The planar side surfaces 276 also facilitate the labelling of the pallets 22 with bar codes 264 (FIG. 1) relating to the product 20 mounted thereon, as described above.

Ideally, the pallets 22 provide both a rigid platform for supporting products 20 to be screened and have minimal impact on heating and/or cooling of the products 20 mounted thereon. Consequently, the pallets 22 are ideally composed of materials which have a high rigidity per unit mass. The materials must be rigid in order to support the products 20 which the pallets 22 will carry, to facilitate various means of attaching the product 20 to the pallet 22, as will be discussed below, and to readily transmit to the products 20 mounted thereon vibrations generated by the vibrating devices 34. Further, materials which have a high rigidity per unit mass allow for rigid pallets 22 which are lightweight to minimize the overall weight that must be borne by the apparatus. Because the amount of thermal energy a body may radiate or absorb is proportional to its mass, it is desirable that the pallets 22 have the minimum possible mass in order to minimize the impact of the pallets 22 on heating or cooling the products 20 mounted thereon. In the preferred embodiment, aluminum and magnesium are well-suited as pallet 22 materials.

In order to further minimize the impact of the pallets 22 on the exchange of thermal energy between the atmosphere of the testing chambers 164 and the products 20 to be screened, the upper surface 266 and side surfaces 276 of the pallets 22 are preferably covered with a layer of insulating material 278. In the preferred embodiment, the insulating material 278 is a fluoro-silicon rubber. The fluoro-silicon rubber layer 278 resists transmission of thermal energy, and provides a skid-resistant surface to aid in maintaining the positioning of a product 20 on the pallet 22. If desired, additional insulation (not shown) may be layered over the upper surface 266 and side surfaces 276 of the pallet 22 to further resist the exchange of thermal energy between the testing chamber 164 and the pallet 22. These layers can be formed to fit around the product 20 being screened so as to insulate the pallet 22 without insulating the product 20 being screened.

In the preferred embodiment, the products 20 are mechanically fastened to the pallets 22 by clamps 280 (FIG. 5), but they may also be secured to the pallets 22 by banding or any other technique appropriate to the size, shape, and nature of the product 20, which will ensure the product 20 will remain secured to the pallet 20 throughout screening.

The overall operation of the environmental screening system is controlled from an operation console 42 (FIG. 1). The console 42 comprises control switches, control logic and monitoring devices necessary to implement and monitor the operation of the screening system, including the entry conveyor 26, the exit conveyor 28, the heating devices 30, the cooling device 32, the vibrating devices 34, the transfer mechanisms 38, the circulation fans 58, the door actuators 92, the flapper valve 114, and the gas pressure sources (not shown). The operation console 42 can be manually-operated or automated in accordance with skills known in the art to suit the particular application. At one extreme, control of all the components may be controlled manually by switches on the panel 42. At another extreme, the operation console 42 may be entirely computer-controlled, and a pre-programmed screening sequence might be initiated upon detection by the bar code reader 262 of the bar codes 264 imprinted of the pallets 22 which may correspond to a preprogrammed screening sequence.

The screening process comprises a number of steps. In the preferred embodiment, the process begins with securing the product 20 to a pallet 22 with clamps 280, connecting any electrical sockets 220 on the product 20 with plugs 218 attached to electrical connectors 216, which electrically connect the sockets 220 on the product 20 to the receptacle 214 mounted on the pallet 22. Once the pallet 22 is loaded, the pallet 22 is placed on the entry conveyor 26, and the entry conveyor 26 is actuated. The commencement of a new screening cycle may be manually activated at the operation console 42 or may be preprogrammed, possibly initiated by the bar code reader 262 detecting bar codes 264 on the pallets 22, which represent preprogrammed screening sequences. The initiation of a screening cycle involves passing each of the products 20 being screened to their next screening phase.

Generally, in each of the compartments 24, the circulation fan 58 is stopped to minimize transmission of thermal energy between the compartments 24 and between the compartments 24 and the ambient environment when the sliding doors 56 are retracted to open doorways 36, thereby minimizing the exchange of thermal energy and resulting temperature degradation between the compartments 24. The actuator arm 40 is engaged to sever the electrical connections between the testing device and the product 20. The first cylinder 234 is extended, then both the first cylinder 234 and the second cylinder 236 are retracted to remove the test plug 224, from the receptacle 214 on the pallet 22. The vacuum ports 144 attaching the lower surface 268 of pallet 22 to the surface of the mounting platform 142 are released. Subsequently, the pneumatic door seals 104 are deflated, and the door actuators 92 are activated, retracting the sliding doors 56 into the recesses 90 in the transverse side walls 66 to open the doorways 36. The transfer mechanism 38 is deployed by the power cylinders 174, lifting the pallet 22 from the mounting platform 142, and the pallet 22 is then rolled by the tractors 172 through the next transfer doorway 36 to transfer the pallet 22 into the next compartment 24. The next pallet 22 on the entry conveyor 26, instead of being moved by the transfer mechanism 38, is rolled by the entry conveyor 26 into the initial compartment 24. In the case of the last compartment 24, the transfer mechanism 38 lifts the pallet 22 from the compartment 24 and rolls it onto the exit conveyor 28.

Once the pallet 22 has encountered the stop 194 indicating that the pallet 22 has reached a predetermined, desired location within the compartment 24, the transfer mechanism 38 is retracted. The sliding doors 56 are closed by the door actuators 92, and the door seals 104 are inflated. The vacuum ports 144 are engaged to attach the pallet 22 to the mounting platform 142, and the actuator arm 40 is extended to allow the test plug 224 on the actuator arm 40 to engage the receptacle 114 on the pallet 22. The heating device 30 or cooling device 32 is activated to reach or restore the desired temperature in the testing chamber 164, and the circulation fan 58 is activated. The vibrating device 34 is activated as desired. Ideally, these steps are all automatically sequenced and closely synchronized in order to minimize the breach of thermal integrity in each of the compartments 24 when the sliding doors 56 are opened.

The independence of the compartments 24 is significant. For example, the testing chamber 164 in one compartment 24 may be heated to a high temperature, and the testing chamber 164 in the adjacent compartment 24 cooled to a very low temperature in order to achieve the most rigorous thermal shock test possible. In addition, one compartment 24 may employ a shaker table 34 vibrating very actively, whereas in the next compartment 24 the shaker table 34 may only be minimally activated or not activated at all. Any desired combination of thermal and/or vibrational stresses can be introduced in this manner.

As can be appreciated with this detailed description, the present invention allows more comprehensive environmental screening than conventional techniques, and makes environmental screening more efficient by reducing the time, manual intervention and energy required to undertake environmental screening. Products 20 can be more comprehensively screened under multiple environmental stimuli, including temperature changes, vibration and other stresses. Further, the environmental screening can be accomplished with greater efficiency. The testing chambers 164 in the compartments 24 are maintained at desired temperatures so that only the products 20 themselves need be heated or cooled to proceed with the screening, and the entire compartment 24 need not be heated or cooled with each screening cycle, saving time and energy. Further, products 20 can be moved between compartments and connected to the screening apparatus with little or no manual intervention, rendering such screening more cost effective.

A presently preferred embodiment of the present invention and many of its improvements have been described with a degree of particularity. This description has been made by way of preferred example. It should be understood, however, that the scope of the present invention is defined by the following claims, and not necessarily by the detailed description of the preferred embodiment.

The embodiments of the invention in which an exclusive property or privilege is claimed are defined as follows:

1. Environmental screening apparatus for screening a product under different screening conditions, comprising:

- a plurality of testing compartments positioned in an array in relation to each other, each of said compartments having an entrance doorway and an exit doorway with a thermally insulated wall separating adjacent compartments in the array, each of said walls having a doorway opening that is both the exit doorway in one of the compartments and the entrance doorway in an adjacent compartment;
- openable and closeable door means positioned in each of said doorway openings for alternately opening and closing said doorway openings;
- temperature control means in each compartment for providing a unique temperature environment in each compartment;
- a platform in each compartment adapted for supporting the product in the compartment;
- vibrating means in said compartments for imparting vibrating motion to the product that is supported by the platform; and
- transfer means adjacent the platform for transporting the product between the compartments when the door means have opened said doorway openings between said compartments.

2. The screening apparatus of claim 1, wherein the temperature control means in at least one of said compartments includes a gas expansion nozzle for introducing a volatile liquid under pressure into the compartment to flash evaporate and cool the compartment by absorbing heat of vaporization, and exhaust means for exhausting excess gas from the compartment to the ambient environment, said exhaust means including a conduit extending from the compartment to the ambient environment with one-way valve means in said conduit for allowing gas to flow only out of the compartment through the conduit.

3. The screening apparatus of claim 2, wherein the compartment has a gas pressure within the compartment and there is an atmospheric pressure of an ambient environment outside the compartment, further wherein said one-way valve means includes a seat, a pivotal flapper closure piece positioned to open and close on said seat, servo means connected to said flapper closure piece for pivoting said flapper closure piece to open or closed position, and control means connected to said servo means for causing said servo means to close said flapper closure means onto said seat so as to maintain said gas pressure within the compartment close to the atmospheric pressure of the ambient environment outside the compartment to prevent gas from flowing back into the compartment.

4. The screening apparatus of claim 3, wherein said one-way valve means includes two seats and two respective flapper closure pieces for opening and closing onto the two seats, and including a link red connected between said two flapper closure pieces in a manner that causes the two flapper closure pieces to open and close in unison.

5. The screening apparatus of claim 2, wherein the temperature control means in the last compartment in the array includes heater means for heating said last compartment in the array to a temperature above ambient temperature such that a product moving sequentially through the compartment in the array is heated above ambient temperature in the last compartment after being cooled below ambient in a compartment preceding the last compartment.

6. The screening apparatus as defined in claim 1, wherein the insulated walls and the door means have thermally insulated cores including at least one layer of fiberglass to resist transmitting thermal energy.

7. The screening apparatus as defined in claim 1, wherein the insulated walls and the door means have acoustically insulated cores including at least one layer of a visco-elastic damper material to resist transmission of vibrations.

8. The screening apparatus of claim 7, wherein said acoustically insulated cores also include a sound decoupling layer of foam.

9. The screening apparatus of claim 7, wherein said acoustically insulated cores also include a sound barrier layer.

10. The screening apparatus as defined in claim 2, wherein said exhaust means further includes a muffler comprising a series of baffles for dampening vibrations carried by gas being released from the compartment.

11. The screening apparatus as defined in claim 1, wherein the temperature control means further includes selectively controllable circulation means for enhancing the exchange of thermal energy between the temperature control means and the compartment.

12. The screening apparatus as defined in claim 11, wherein the circulation means further includes a fan means for facilitating the exchange of thermal energy between the temperature control means and the compartment.

13. The screening apparatus as defined in claim 12, wherein the circulation means further includes baffling means to enhance circulation within the compartment.

14. The screening apparatus of claim 13, wherein said baffling means includes smoothly rounded air deflectors positioned in corners where walls intersect.

15. The screening apparatus of claim 13, wherein said baffling means includes a partial partition extending partially across the compartment between the fan means and the platform when the platform is positioned in the compartment.

16. The screening apparatus of claim 13, wherein said baffling means comprises curved corner baffles positioned in upper corners of the compartment.

17. The screening apparatus of claim 13, wherein said baffling means includes an elongated channel means with curved lateral edges positioned to extend through the compartment between said fan means and said vibrating means.

18. The screening apparatus as defined in claim 1, including:

door actuator means for opening and closing at least some of the door means; and door sealing means for releasably sealing at least some of the door means when the door means are in position to close the doorway openings.

19. The screening apparatus as defined in claim 1, further including retracting means operatively associated with said transfer means for selectively removing and said transfer means from engagement with the product when the product is being screened in the compartment.

20. The screening apparatus as defined in claim 1, further comprising an operation console operatively connected to the temperature control means, the vibrating means, and the transfer means.

21. The screening apparatus of claim 1, wherein said testing compartments are positioned in a linear array.

22. The screening apparatus of claim 1, wherein each of said compartments includes an additional thermally insulated wall that does not separate adjacent compartments and that does not include a doorway opening, said additional thermally insulated wall including a window comprising multiple transparent juxtaposed panes positioned in spaced-apart relation to define multiple spaces separated by said panes such that each of said spaces has a different distance between panes than the other spaces.

23. The screening apparatus of claim 22, including seven spaced-apart panes that are spaced at intervals relative to a base unit of measure at a relative spacing of 1.0, 1.1, 1.2, 1.3, 1.4, and 1.5 units.

24. The screening apparatus of claim 1, including plug receptacle means on said platform and plug means in the compartment for making an electrical connection of electric test equipment to the platform, said product also being electrically connectable to said plug receptacle means.

25. The screening apparatus of claim 24, wherein said plug means includes extension and retraction means for extending said plug means into electrical contact with said plug receptacle means and for retracting said plug means away from said plug receptacle means.

26. The screening apparatus of claim 25, wherein said extension and retraction means includes alignment means for aligning said plug means with said plug receptacle means.

27. The screening apparatus of claim 26, wherein said alignment means includes a conical protrusion adjacent said plug means and a conical socket adjacent said plug receptacle means for receiving said conical protrusion and thereby moving said plug means into alignment with said plug receptacle means.

28. The screening apparatus of claim 27, including guide extension and retraction means connected to said conical protrusion for extending and retracting said conical protrusion independent of said plug means.

29. The screening apparatus of claim 1, wherein said transfer means includes tractor means for engaging the product and causing the product to move into the compartment when the entrance door is opened, for disengaging the product when both the entrance door and the exit door are closed with the product in the compartment, and for engaging the product and causing the product to move out of the compartment when the exit door is opened.

30. The screening apparatus of claim 29, wherein said tractor means includes a revolving track belt configured with a path surface that is liftable into engagement with a portion of the product that is positioned over the track belt and wherein revolving movement of the track belt is imparted to the product to propel the product when the track belt is engaged with the product.

31. The screening apparatus of claim 30, including retractable stop means in the compartment for extending into a path of travel of the product being propelled by the track belt to stop movement of the product in the compartment and for retracting from the path of travel to allow movement of the product out of the compartment.

32. Environmental screening apparatus for screening a product under different screening conditions, comprising:

a plurality of testing compartments positioned in an array in relation to each other, each of said compartments having an entrance doorway and an exit doorway with a thermally insulated wall separating adjacent compartments in the array, each of said walls having a doorway opening that is both the exit doorway in one of the compartments and the entrance doorway in an adjacent compartment, each of said compartments also having a gas pressure within the compartment and an atmospheric pressure of an ambient environment outside the compartment;

openable and closeable door means positioned in each of said doorway openings for alternately opening and closing said doorway openings;

temperature control means in each compartment for providing a unique temperature environment in each compartment, wherein the temperature control means in at least one of the compartments includes a gas expansion nozzle for introducing liquid under pressure into the compartment to flash evaporate and cool the compartment by absorbing heat of vaporization, and exhaust means for exhausting gas from the compartment to the ambient environment outside the compartment, said exhaust means including a conduit extending from the compartment to the ambient environment with one-way valve means in said conduit for allowing gas to flow only out of the compartment through the conduit, wherein said one-way valve means includes a seat, a pivotal flapper closure piece positioned to open and close on said seat, servo means connected to said flapper closure piece for pivoting said flapper closure piece to open or closed position, and control means connected to said servo means for causing said servo means to close said flapper closure means onto said seat so as to maintain said gas pressure within the compartment close to the atmospheric pressure of the ambient environment outside the compartment to prevent gas from flowing back into the compartment;

pallet means for mounting and carrying the product sequentially through the compartments in the array;

vibrating means in said compartments for imparting vibrating motion to said pallet means; and transfer means operatively engageable with the pallet means for transporting the pallet means and the product mounted on the pallet means between the compartments when the door means have opened said doorway openings between said compartments.

33. The screening apparatus of claim 32, wherein said one-way valve means includes two seats and two respective flapper closure pieces for opening and closing onto the two seats, and including a link rod connected between said two flapper closure pieces in a manner that causes the two flapper closure pieces to open and close in unison.

\* \* \* \* \*